United States Patent
Porta et al.

(10) Patent No.: US 8,741,903 B2
(45) Date of Patent: Jun. 3, 2014

(54) ORGANIC COMPOUND FOR USE IN THE TREATMENT OF HEPATOCELLULAR CANCER (HCC)

(75) Inventors: Diana Graus Porta, Basel (CH); Herbert Schmid, Neuenburg (DE); Michael Shi, East Hanover, NJ (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 13/641,668

(22) PCT Filed: Apr. 14, 2011

(86) PCT No.: PCT/EP2011/055906
§ 371 (c)(1),
(2), (4) Date: Dec. 4, 2012

(87) PCT Pub. No.: WO2011/128403
PCT Pub. Date: Oct. 20, 2011

(65) Prior Publication Data
US 2013/0123272 A1    May 16, 2013

Related U.S. Application Data

(60) Provisional application No. 61/324,936, filed on Apr. 16, 2010.

(51) Int. Cl.
*A61K 31/496* (2006.01)
(52) U.S. Cl.
USPC ................................................. 514/253.07
(58) Field of Classification Search
CPC ............. A61K 31/4709; A61K 31/496; C07D 215/227
USPC ................................................... 514/253.07
See application file for complete search history.

(56) References Cited

U.S. PATENT DOCUMENTS

2006/0183750 A1 *  8/2006  Menezes et al. ......... 514/253.07

FOREIGN PATENT DOCUMENTS

| WO | WO 2005/082340 | * | 9/2005 | ............ A61K 31/00 |
| WO | WO 2006/081445 | | 8/2006 | |

OTHER PUBLICATIONS

Huynh et al., "Molecularly targeted therapy in hepatocellular carcinoma", Biochemical Pharmacology, vol. 80, No. 5, pp. 550-560, 2010.
M. Shi et al., (ONC-10-147) Davitinib (TKI258), a novel oral multikinase inhibitor demonstrates anti-tumor and antiangiogenic activities in xenograft models of human hepatocellular carcinoma Running title: TKI258 suppresses HCC growth.

* cited by examiner

*Primary Examiner* — Savitha Rao
*Assistant Examiner* — Angela Brown-Pettigrew
(74) *Attorney, Agent, or Firm* — Gregory Ferraro

(57) ABSTRACT

The present invention relates to the method of treating hepatocellular cancer (HCC) with 4-amino-5-fluoro-3-[6-(4-methylpiperazin-1-yl)-1H-benzimidazol-2-yl]-1H-quinolin-2-one or a pharmaceutically acceptable salt or a tautomer thereof, or a hydrate or a solvate.

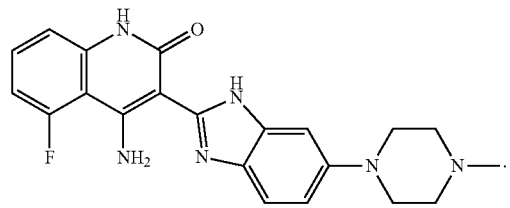

1 Claim, 4 Drawing Sheets

ORGANIC COMPOUND FOR USE IN THE TREATMENT OF HEPATOCELLULAR CANCER (HCC)

Figure 1:
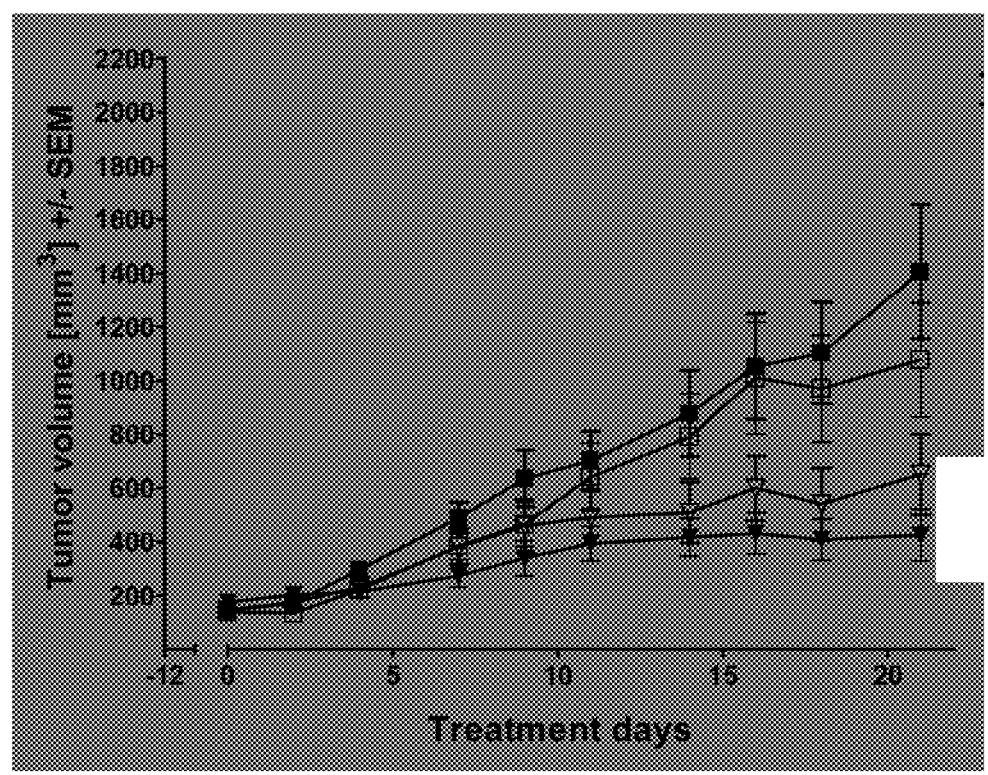

This application is a 371 of PCT/EP2011/055906 filed on Apr. 14, 2011, which claims benefit of U.S. Provisional Application No. 61/324,936, filed on Apr. 16, 2010, which in its entirety is herein incorporated by reference.

The invention relates to the use of 4-amino-5-fluoro-3-[6-(4-methylpiperazin-1-yl)-1H-benzimidazol-2-yl]-1H-quinolin-2-one, or a tautomer thereof or a pharmaceutically acceptable salt thereof or a hydrate thereof or a solvate thereof for the manufacture of pharmaceutical compositions for use in the treatment of hepatocellular carcinoma or liver cancer (HCC) or liver cancer, to the use of 4-amino-5-fluoro-3-[6-(4-methylpiperazin-1-yl)-1H-benzimidazol-2-yl]-1H-quinolin-2-one in the treatment of hepatocellular cancer or liver cancer.

Management of hepatocellular carcinoma (HCC) or liver cancer is a major problem. HCC development and progression is highly dependent on angiogenesis. VEGF (vascular endothelial growth factor), fibroblast growth factor (FGF) and platelet-derived growth factor (PDGF) and their receptors are associated with HCC neovascularization. Overexpression of FGFR3 (fibroblast growth factor receptor 3) has been described in HCC.

Currently there are limited treatment options for advanced HCC patients. Until now there is only one treatment approved for HCC, namely sorafenib. The patients and physicians are thus clearly lacking alternative treatments, especially for patients that have unresectable HCC, that are not eligible for surgery, that are not eligible for locoregional surgery or that faced disease progression after surgery. Said patients are in such a situation that they do no longer have alternative therapies. Despite the merits of sorafenib, the median overall survival for the patients does not extend beyond a year. The median overall survival from the 1st line sorafenib treatment in patients with unresectable HCC was 10.7 months (Llovet et al, N Engl J Med; 2008, 359: 378-390), and even shorter in HCC patients of Asia-Pacific region with a median overall survival of 6.5 months (Cheng et al, 2009, Lancet Oncol 10: 25-34). There is no effective approved treatment for advanced HCC patients who have progressed on sorafenib treatment. Based on published data, it is assumed that the median overall survival is around 5 months in HCC patients who have progressed on or after sorafenib treatment as second line treatment, e.g. after surgery. Moreover, there is a need to monitor and manage, when possible, side effects associated with this treatment, such as for example hypertension and hand-foot syndrome (HFS) or hand-foot skin reaction (HFSR).

There is thus an unmet medical need for better systemic therapy for this patient population exhibiting a high mortality and morbidity.

It has now been found that 4-amino-5-fluoro-3-[6-(4-methylpiperazin-1-yl)-1H-benzimidazol-2-yl]-1H-quinolin-2-one or a pharmaceutically acceptable salt or a hydrate or a solvate can solve theses problems, as it efficiently reduced tumor volume in animal models for hepatocellular carcinoma (HCC) or liver cancer and thus provides a new treatment option for HCC or liver cancer. Said treatment is advantageous as it allows to bringing further treatment option to a category of patients that were previously lacking treatment or lacking such treatment options. For example some patient might not have been able to undergo treatment with the current approved therapy, e.g. sorafenib, because of underlying conditions that render said treatment not appropriate for the patient, such as patient having HCC refractory to the approved drug, or non responsive to said drug, and/or patients that are intolerant or that would face some side effects such as hypertensive patients, patients developing hand-foot syndrome (HFS) or hand-foot skin reaction (HFSR) over another medicine, e.g. with sorafenib treatment.

4-Amino-5-fluoro-3-[6-(4-methylpiperazin-1-yl)-1H-benzimidazol-2-yl]-1H-quinolin-2-one or a pharmaceutically acceptable salt or a hydrate or a solvate has the structure shown in Formula I:

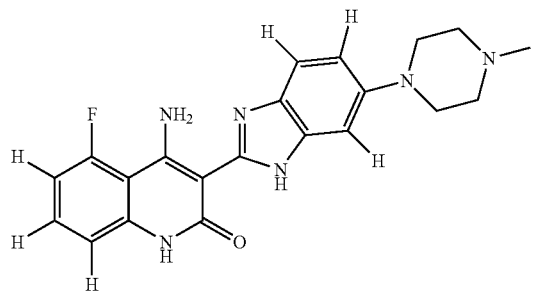 [SMILES: CN1CCN(c2ccc3nc(-c4c(N)c5c(F)cccc5[nH]c4=O)[nH]c3c2)CC1]

The compound of Formula I inhibits various protein kinases, such as tyrosine receptor kinases (RTKs). Consequently, the compound of Formula I and its salts are useful for inhibiting angiogenesis and treating proliferative diseases, e.g. hepatocellular carcinoma or liver cancer. Preparation of this compound and its salts, including the mono-lactic acid salt, are described in U.S. Pat. Nos. 6,605,617, 6,774,237, 7,335,774, and 7,470,709, and in U.S. patent application Ser. Nos. 10/982,757, 10/982,543, and 10/706,328, and in the published PCT applications WO 2006/127926 and WO2009/115562, each of which is incorporated herein by reference in its entirety.

The mono-lactate salt of the compound of Formula I exist in a variety of polymorphs, including, e.g., the monohydrate form and the anhydrous form. Polymorphs occur where the same composition of matter (including its hydrates and solvates) crystallizes in a different lattice arrangement resulting in different thermodynamic and physical properties specific to the particular crystalline form.

Receptor tyrosine kinases (RTKs) are transmembrane polypeptides that regulate developmental cell growth and differentiation, remodeling and regeneration of adult tissues. Polypeptide ligands known as growth factors or cytokines, are known to activate RTKs. Signaling RTKs involves ligand binding and a shift in conformation in the external domain of the receptor resulting in its dimerization. Binding of the ligand to the RTK results in receptor trans-phosphorylation at specific tyrosine residues and subsequent activation of the catalytic domains for the phosphorylation of cytoplasmic substrates.

The compound of formula I inhibits tyrosine kinases. The tyrosine kinase may be but not limited to Cdc2 kinase (cell division cycle 2 kinase), Fyn (FYN oncogene kinase related to SRC, FGR, YES), Lck (lymphocyte-specific proetein tyrosine kinase), c-Kit (stem cell factor receptor or mast cell growth factor receptor), p60src (tyrosine kinase originally identified as the v-src oncogene of the rous sarcoma viurs), c-ABL (tyrosine kinase that stands for an oncogene product originally isolated from the Adelson leukemia yin's), VEGFR3, PDGFRα (platelet derived growth factor receptor α), PDGFRβ (platelet derived growth factor receptor β), FGFR3 (fibroblast growth factor receptor 3), FLT-3 (fins-like tyrosine kinase-3), or Tie-2 (tyrosine kinase with 1 g and EGF homology domains). In some embodiments, the tyrosine kinase is Cdc2 kinase, Fyn, Lck, or Tie-2 and in some other embodiments, the tyrosine kinase is c-Kit, c-ABL, p60src, VEGFR3, PDGFRα, PDGFRβ, FGFR3, or FLT-3.

Two subfamilies of RTKs are specific to the vascular endothelium. These include the vascular endothelial growth factor (VEGF) subfamily and the Tie receptor subfamily. Class III RTKs include vascular endothelial growth factor receptor 1 (VEGFR-1), vascular endothelial growth factor receptor 2 (VEGFR-2), and vascular endothelial growth factor receptor 3 (VEGFR-3).

The present invention provides the use of 4-amino-5-fluoro-3-[6-(4-methylpiperazin-1-yl)-1H-benzimidazol-2-yl]-1H-quinolin-2-one or a tautomer thereof, or a mixture thereof, or a pharmaceutically acceptable salt or a hydrate or a solvate for the manufacture of pharmaceutical compositions for use in the treatment of hepatocellular carcinoma or liver cancer, for example advanced hepatocellular carcinoma, Barcelona HCC Stage C, for example in HCC patients that have hypertension, in HCC patients that have developed or develop hand-foot syndrome or a hand-foot skin reaction, e.g. under another treatment, e.g. under sorafenib treatment, in patient that have unresectable HCC, in patients, that are not eligible for surgery, that are not eligible for locoregional surgery or that faced disease progression, e.g. after any of the former mentioned treatment, or patient that are intolerant or resistant to another HCC or liver cancer therapy, e.g. patients having an HCC resistant to sorafenib, or patient having an HCC not responding to sorafenib or patient that are intolerant to sorafenib.

Indeed side effects associated with a therapeutic treatment raise patients discomfort and some patients can even be reluctant to take the treatment. When there is a Hand-Foot syndrome for example, chemotherapy treatment may need to be interrupted or the dose adjusted, e.g. lowered, to prevent the worsening of the hand-foot syndrome, resulting in the HHC condition of the patient not being longer adequately controlled. On top of this the side-effects requires additional costs to monitor and manage them.

According to the present invention, 4-amino-5-fluoro-3-[6-(4-methylpiperazin-1-yl)-1H-benzimidazol-2-yl]-1H-quinolin-2-one or a pharmaceutically acceptable salt thereof or a tautomer thereof, or a mixture thereof is use as the sole active against HCC.

The present invention further provides is 4-amino-5-fluoro-3-[6-(4-methylpiperazin-1-yl)-1H-benzimidazol-2-yl]-1H-quinolin-2-one or a pharmaceutically acceptable salt or a tautomer thereof, or a hydrate or a solvate for use in treating hepatocellular carcinoma or liver cancer. According to the present invention, Compound I refers to 4-amino-5-fluoro-3-[6-(4-methylpiperazin-1-yl)-1H-benzimidazol-2-yl]-1H-quinolin-2-one or a pharmaceutically acceptable salt or a tautomer thereof, or a hydrate or a solvate thereof, for example to 4-amino-5-fluoro-3-[6-(4-methylpiperazin-1-yl)-1H-benzimidazol-2-yl]-1H-quinolin-2-one, or a tautomer thereof, for example in its lactate salt form.

In some embodiments, the present invention pertains to a method of treating humans suffering from hepatocellular carcinoma or liver cancer which comprises administering to said human in need of such treatment a dose of 4-amino-5-fluoro-3-[6-(4-methylpiperazin-1-yl)-1H-benzimidazol-2-yl]-1H-quinolin-2-one or a tautomer thereof, or a pharmaceutically acceptable salt or a hydrate or a solvate is provided.

In a further aspect the present invention provides a pharmaceutical preparation for the treatment of hepatocellular carcinoma or liver cancer comprising 4-amino-5-fluoro-3-[6-(4-methylpiperazin-1-yl)-1H-benzimidazol-2-yl]-1H-quinolin-2-one, or a tautomer thereof, or a pharmaceutically acceptable salt or a hydrate or a solvate.

Depending on species, age, individual condition, mode of administration, and the clinical picture in question, effective doses for example weekly doses of about 200 to 3000 mg, of 4-amino-5-fluoro-3-[6-(4-methylpiperazin-1-yl)-1H-benzimidazol-2-yl]-1H-quinolin-2-one or a pharmaceutically acceptable salt, or a tautomer thereof, or a hydrate or a solvate are administered to a human, for example at a dose of 2500 mg per week. Said administration can be made for example as follows the dose is taken by the patient 5 days per week followed by two days where the patient does not take the treatment. According to the present invention, Compound I or a tautomer thereof can be administered to a patient at a weekly dose of 2500 mg, for example the patient is administered with Compound of formula I 500 mg for 5 days followed by two days without treatment. The daily dose can be administered as two single doses of 250 mg for example.

The present invention further provides a method for administering to a human having hepatocellular carcinoma or liver cancer 4-amino-5-fluoro-3-[6-(4-methylpiperazin-1-yl)-1H-benzimidazol-2-yl]-1H-quinolin-2-one or a tautomer thereof, or a pharmaceutically acceptable salt or a hydrate or a solvate to a human subject about once weekly or more frequently.

The present invention provides 4-Amino-5-fluoro-3-[6-(4-methylpiperazin-1-yl)-1H-benzimidazol-2-yl]-1H-quinolin-2-one or a pharmaceutically acceptable salt, or tautomer thereof, or mixture thereof, or a hydrate or a solvate thereof for use to improve, in a patient population having HCC, the median overall survival, wherein in said patient population the median overall survival is at least superior or equal to 11 months, superior or equal to 12 months, superior or equal to 13 months and wherein 4-Amino-5-fluoro-3-[6-(4-methylpiperazin-1-yl)-1H-benzimidazol-2-yl]-1H-quinolin-2-one or a pharmaceutically acceptable salt, or tautomer thereof or a mixture thereof, or a hydrate or a solvate thereof is administered to said patients per os at a 500 mg dose on a 5 days on/2 days off weekly schedule, e.g. said patients are for example patients who are not eligible for or had disease progression after surgical or locoregional therapies, Barcelona HCC Stage C patients, patients having unresectable HCC, HCC patient that has hypertension and/or HFS or HFSR.

SHORT DESCRIPTION OF THE FIGURES

FIG. 1/4 shows the in vivo inhibition of HUH7 human HCC xenografts by TKI258. ■ is Vehicle 10 mL/kg p.o. qd, ⊟ is TKI258 10 mg/kg p.o. qd, ▽ is 30 mg/kg p.o. qd, ▼ is 50 mg/kg p.o. qd.

Figure 2:
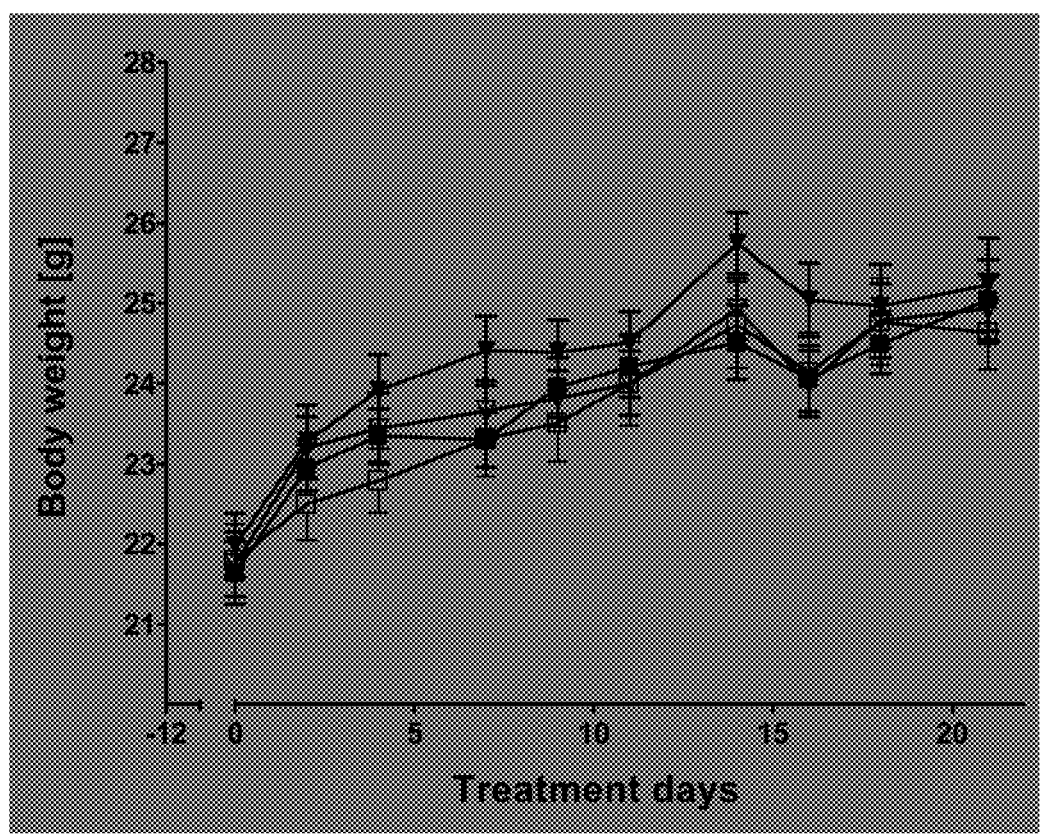

FIG. 2/4 shows the body weight of the animals with the HUH7 human HCC xenografts treated by TKI258. ■ is Vehicle 10 mL/kg p.o. qd, ⊟ is TKI258 10 mg/kg p.o. qd, ▽ is 30 mg/kg p.o. qd, ▼ is 50 mg/kg p.o. qd.

Figure 3:
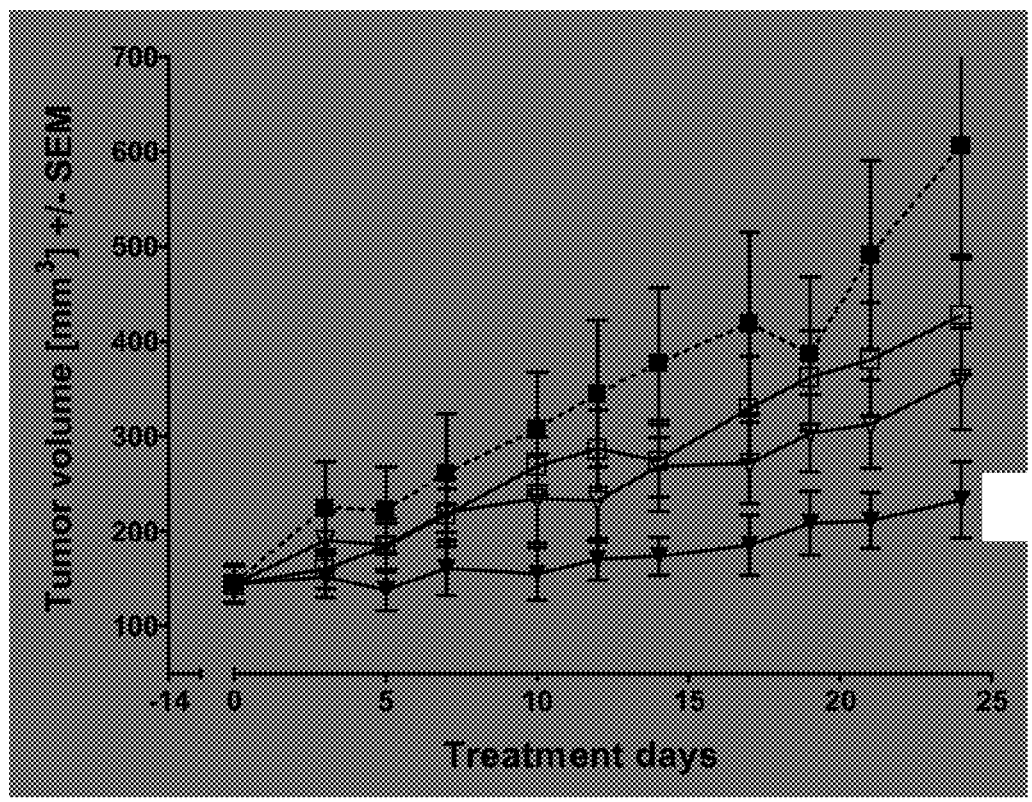

FIG. 3/4 shows the in vivo inhibition of PLC/PFR/5 human HCC xenografts. ■ is Vehicle 10 mL/kg p.o. qd, ⊟ is TKI258 10 mg/kg p.o. qd, ▽ is 30 mg/kg p.o. qd, ▼ is 50 mg/kg p.o. qd.

Figure 4:
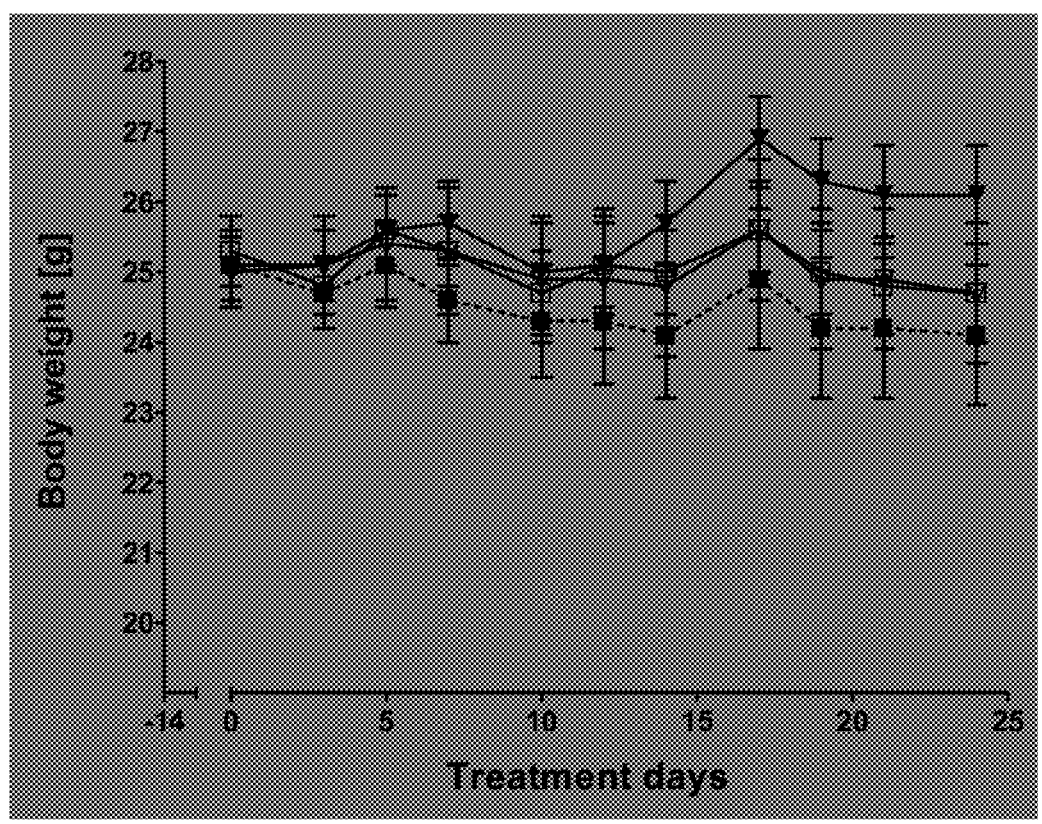

FIG. 4/4 shows the body weight of the animals with the PLC/PFR/5 human HCC xenografts treated by TKI258. ■ is Vehicle 10 mL/kg p.o. qd, ⊟ is TKI258 10 mg/kg p.o. qd, ▽ is 30 mg/kg p.o. qd, ▼ is 50 mg/kg p.o. qd.

Following is a description by way of examples.

EXAMPLE 1

HUH-7 tumors are established by subcutaneous injection of $5 \times 10^6$ cells in 100 μl Hank's Balanced Salt Solution (HBSS) from Sigma containing 50% Basement Membrane Matrix (BD Matrigel) into the right flank of nude mice. The parental HUH-7 hepatoma cell line is initially derived from a male human liver carcinoma. HUH-7 cells are cultured in RPMI 1640 medium supplemented with 10% Fetal Calf Serum, 5% horse serum, 1% L-glutamine and 1% Penecyllin/Streptavidin. Cell culture reagents are purchased from BioConcept (Allschwil, Switzerland).

12 days after the injection of tumor cells the tumor volumes are 138±24 mm$^3$. At this time (day 1 of the study) the treatment with Compound I starts Animals are euthanized after 21 days of consecutive daily treatments 24 h after the last compound administration. Body weights and tumor volumes are recorded three times a week. Tumor volumes are measured with calipers and determined according to the formula length×width×hight×π/6. In addition to presenting changes of tumor volumes over the course of treatments, antitumor activity is expressed as ΔT/ΔC % (mean change of tumor volume of treated animals/mean change of tumor volume of control animals)×100.

Compound I is formulated by dispersing the compound in water and vortexed until a clear solution is obtained. Compound is applied daily by oral gavage at the concentration of 10, 30 and 50 mg/kg, free base equivalents. Each group contains 8 animals. Vehicle-treated animals receive a daily oral administration of water. The application volumes in all experiments were 10 ml/kg.

Where applicable, data are presented as mean±SEM. For all tests, the level of significance is set at $p<0.05$. For the mean increase in tumor size, comparisons between groups and vehicle control group are done using one-way ANOVA followed by Dunnett's test. The level of significance of body weight change within a group between the start and the end of the experiment is determined using a paired t-test. The significance of body weight changes between the treatment group and the vehicle control group is determined with a one-way ANOVA followed by Dunnett's test. Calculations are performed using GraphPad Prism 5.0 (GraphPad Software Inc.).

FIG. 1/4 shows the dose-dependent inhibition of tumor growth, which was statistically significant at 30 and 50 mg/kg, with % T/C of 75, 40 and 20 respectively. The treatment with these doses of the compound was well tolerated as indicated by an increase in body weight over the course of treatment which was similar for the vehicle treated as well as the compound treated groups of animals (FIG. 2/4).

EXAMPLE 2

PLC/PFR/5 tumors are established by subcutaneous injection of 5×10$^6$ cells in 100 μl Hank's Balanced Salt Solution (HBSS) from Sigma containing 50% Basement Membrane Matrix (BD Matrigel) into the right flank of female nude mice. The parental PLC/PFR/5 cell carcinoma cell line is initially derived from a male patient with liver carcinoma. PLC/PFR/5 cells are cultured in RPMI 1640 medium supplemented with 10% Fetal Calf Serum, 5% horse serum, 1% L-glutamine and 1% penecyllin/Streptavidin. Cell culture reagents are purchased from BioConcept (Allschwil, Switzerland).

14 days after the injection of tumor cells the tumor volumes are 145±20 mm$^3$. At this time (day 1 of the study) the treatment with Compound I starts. Animals are euthanized after 24 days of consecutive daily treatments 24 h after the last compound administration. Body weights and tumor volumes are recorded three times a week. Tumor volumes are measured with calipers and determined according to the formula length×width×hight×π/6. In addition to presenting changes of tumor volumes over the course of treatments, antitumor activity is expressed as ΔT/ΔC % (mean change of tumor volume of treated animals/mean change of tumor volume of control animals)×100.

Compound I is formulated by dispersing the compound in water and vortexed until a clear solution is obtained. The compound is applied daily by oral gavage at the concentration of 10, 30 and 50 mg/kg, free base equivalents. Each group contains 8 animals Vehicle-treated animals receive a daily oral administration of water. The application volumes in all experiments are 10 ml/kg.

Where applicable, data are presented as mean±SEM. For all tests, the level of significance is set at $p<0.05$. For the mean increase in tumor size, comparisons between groups and vehicle control group are done using one-way ANOVA followed by Dunnett's test. The level of significance of body weight change within a group between the start and the end of the experiment is determined using a paired t-test. The significance of body weight changes between the treatment group and the vehicle control group is determined with a one-way ANOVA followed by Dunnett's test. Calculations are performed using GraphPad Prism 5.0 (GraphPad Software Inc.).

FIG. 3/4 shows dose-dependent inhibition of tumor growth, which was statistically significant at 50 mg/kg, with % T/C of 67, 47 and 19 respectively. The treatment with these doses of the compound had no significant effect on body weight as compared to the vehicle-treated group (FIG. 4/4).

EXAMPLE 3

A Study of Dovitinib versus Sorafenib in Adult Patients with Hepatocellular Carcinoma (HCC) as a First Line Treatment Study design A randomized phase II open label, multicenter study in the Asia pacific region to compare safety and efficacy of Compound I versus sorafenib as 1$^{st}$ line treatment in patients with advanced HCC.

About 150 patients will be randomized (1:1 ratio). Patients receive Compound T or sorafenib until disease progression or unacceptable toxicities. Tumor assessments, safety monitoring follow the protocol.

Patient population: adult patients with advanced HCC who are nor eligible or had disease progression after surgical or locoregional therapies.

Primary objective: treatment effect of Compound I versus sorafenib on overall survival.

Secondary objective: assessment of the two treatment arms with respect to time to tumor progression Study treatment: Compound I 500 mg, 5 days on/2 days off, Sorafenib 400 mg per os.

EXAMPLE 4

A randomized, double blinded placebo study to evaluate efficacy and safety of plus best supportive care versus placebo plus best supportive care in adults with advanced HCC after failure of sorafenib treatment.

Study design A randomized Phase II, double-blind, placebo-controlled, international study comparing the safety and efficacy of Compound I/BSC to placebo/BSC in patients with advanced HCC who were previously treated with sorafenib and whose disease progressed while on or after sorafenib treatment.

About 150 patients are randomized (2:1 ratio) according to ECOG (0 vs. 1 or 2). Patients receive Compound I/BSC or placebo/BSC until disease progression, or unacceptable toxicities. Tumor assessments, safety monitoring and other study procedures should follow protocol defined schedule. Interim analysis will not be performed.

Patient population: Adult patients with histologically or cytologically confirmed diagnosis of HCC whose disease progressed while on or after sorafenib treatment Primary objective: To estimate the treatment effect of Compound I/BSC vs. placebo/BSC overall survival in patients with advanced HCC whose disease progressed while on or after sorafenib treatment or who are intolerant to sorafenib.

Key secondary objective: To assess the two treatment arms with respect to time to progression (TTP) (radiologic assessment).

Key exclusion criteria: Patients who have received any systemic treatment with investigational agents or targeted therapy for HCC (except for sorafenib)

Study treatment: Compound I (500 mg, 5 days on/2 days off)/BSC, Control refers to matching placebo/BSC.

The invention claimed is:

1. A method of treating humans suffering from hepatocellular carcinoma (HCC) which comprises administering to said human in need of such treatment a dose of 4-amino-5-fluoro-3-[6-(4-methylpiperazin-1-yl)-1H-benzimidazol-2-yl]-1H-quinolin-2-one or a tautomer thereof, or a pharmaceutically acceptable salt or a hydrate or a solvate thereof wherein 4-amino-5-fluoro-3-[6-(4-methylpiperazin-1-yl)-1H-benzimidazol-2-yl]-1H-quinolin-2-one or a tautomer thereof or a pharmaceutically acceptable salt or a hydrate or a solvate thereof is used as the sole active ingredient, wherein the weekly dose consists of a daily dose administration of 500 mg for 5 days and no administration for two days.

* * * * *